(12) United States Patent  (10) Patent No.: US 8,047,201 B2
Guyuron et al.  (45) Date of Patent: Nov. 1, 2011

(54) NASAL DILATOR

(75) Inventors: Bahman Guyuron, Lyndhurst, OH (US); Daniel Puthoff, Westlake, OH (US); Jamie Horvath, Lakewood, OH (US); Paul Tamulewicz, Cleveland, OH (US)

(73) Assignee: Innovation Alley Design, LLC, Lyndhurst, OH (US)

( * ) Notice: Subject to any disclaimer, the term of this patent is extended or adjusted under 35 U.S.C. 154(b) by 1244 days.

(21) Appl. No.: 11/380,460

(22) Filed: Apr. 27, 2006

(65) Prior Publication Data
US 2007/0255309 A1 Nov. 1, 2007

(51) Int. Cl.
A61M 15/00 (2006.01)
A61M 16/00 (2006.01)
A62B 7/00 (2006.01)
A62B 9/00 (2006.01)
A62B 18/00 (2006.01)

(52) U.S. Cl. ........... 128/200.24; 128/848; 606/199; 606/204.45

(58) Field of Classification Search ......... 128/200.24, 128/858, 848; 606/199, 213, 191, 196, 201, 606/204.45; 602/42, 41, 61
See application file for complete search history.

(56) References Cited

U.S. PATENT DOCUMENTS

| 4,414,977 | A | | 11/1983 | Rezakhany |
| D310,565 | S | | 9/1990 | Petruson |
| 5,213,565 | A | * | 5/1993 | Rollband ............... 602/41 |
| 5,476,091 | A | | 12/1995 | Johnson |
| 5,479,944 | A | * | 1/1996 | Petruson ............... 128/858 |
| 5,533,499 | A | | 7/1996 | Johnson |
| 5,533,503 | A | | 7/1996 | Doubek et al. |
| 5,546,929 | A | | 8/1996 | Muchin |
| 5,549,103 | A | | 8/1996 | Johnson |
| 5,553,605 | A | | 9/1996 | Muchin |
| RE35,408 | E | | 12/1996 | Petruson |
| 5,611,333 | A | | 3/1997 | Johnson |
| 5,611,334 | A | | 3/1997 | Muchin |
| D379,513 | S | | 5/1997 | Ierulli |
| D380,264 | S | | 6/1997 | Petruson |
| 5,653,224 | A | | 8/1997 | Johnson |
| 5,665,104 | A | | 9/1997 | Lee |
| 5,669,377 | A | | 9/1997 | Fenn |
| D388,172 | S | | 12/1997 | Cipes |
| 5,706,800 | A | | 1/1998 | Cronk et al. |

(Continued)

FOREIGN PATENT DOCUMENTS
EP 0 909 151 4/1997
(Continued)

*Primary Examiner* — Justine Yu
*Assistant Examiner* — Colin W Stuart
(74) *Attorney, Agent, or Firm* — Renner, Otto, Boisselle & Sklar, LLP

(57) ABSTRACT

A nasal dilator that includes an upper resilient member for dilating the nasal valve and a lower resilient member for dilating the nostrils. The upper resilient member and lower resilient member may be attached to one another by a flexible substrate having a middle portion that is narrower in length than the upper or lower resilient members. The nasal dilator also may have adhesive tabs extending downwardly from the lower portion of the substrate on either side of the nose and towards the nostril entry, for temporary attachment to the side of the nasal vestibule to reduce nostril collapse. The nasal dilator also may include bendable or configurable hooks extending downwardly from the lower portion of the substrate and towards the nostril entrance for insertion into the nostril to reduce nostril collapse.

17 Claims, 9 Drawing Sheets

U.S. PATENT DOCUMENTS

| | | | |
|---|---|---|---|
| 5,718,224 | A | 2/1998 | Muchin |
| 5,735,272 | A | 4/1998 | Dillon et al. |
| 5,755,232 | A * | 5/1998 | Kalt .............................. 128/845 |
| 5,769,089 | A * | 6/1998 | Hand et al. .................... 128/858 |
| 5,816,241 | A | 10/1998 | Cook |
| 5,817,039 | A | 10/1998 | Raunig |
| 5,890,486 | A | 4/1999 | Mitra et al. |
| 5,895,409 | A | 4/1999 | Mehdizadeh |
| 5,922,006 | A | 7/1999 | Sugerman |
| 5,931,854 | A | 8/1999 | Dillon |
| 5,957,126 | A | 9/1999 | Neeser |
| 5,961,537 | A | 10/1999 | Gould |
| 5,976,173 | A | 11/1999 | Berke |
| 6,006,746 | A | 12/1999 | Karell |
| 6,029,658 | A | 2/2000 | De Voss |
| D422,358 | S | 4/2000 | Lundy, Jr. et al. |
| D422,702 | S | 4/2000 | Lundy, Jr. et al. |
| D422,703 | S | 4/2000 | Lundy, Jr. et al. |
| 6,058,931 | A | 5/2000 | Muchin |
| 6,065,470 | A | 5/2000 | Van Cromvoirt et al. |
| 6,080,179 | A | 6/2000 | Gould |
| 6,093,169 | A | 7/2000 | Cardoso |
| 6,098,616 | A | 8/2000 | Lundy, Jr. et al. |
| 6,196,228 | B1 | 3/2001 | Kreitzer et al. |
| 6,228,101 | B1 | 5/2001 | Stratton |
| 6,238,411 | B1 | 5/2001 | Thorner |
| 6,244,265 | B1 | 6/2001 | Cronk et al. |
| 6,270,512 | B1 | 8/2001 | Rittmann |
| 6,276,360 | B1 | 8/2001 | Cronk et al. |
| 6,318,362 | B1 | 11/2001 | Johnson |
| 6,328,754 | B1 | 12/2001 | Marten et al. |
| 6,357,436 | B1 | 3/2002 | Kreitzer et al. |
| 6,375,667 | B1 | 4/2002 | Ruch |
| 6,390,089 | B1 * | 5/2002 | Lacouture ................ 128/200.24 |
| 6,419,687 | B1 | 7/2002 | Berke |
| 6,453,901 | B1 * | 9/2002 | Ierulli ...................... 128/200.24 |
| 6,470,883 | B1 | 10/2002 | Beaudry |
| 6,478,023 | B1 | 11/2002 | Lockwood |
| 6,570,051 | B1 | 5/2003 | Beaudry |
| 6,603,051 | B1 | 8/2003 | Beaudry |
| 6,631,714 | B2 | 10/2003 | Von Duyke et al. |
| 6,663,649 | B2 | 12/2003 | Stratton |
| 6,669,712 | B1 | 12/2003 | Cardoso |
| 6,694,970 | B2 * | 2/2004 | Spinelli et al. ........... 128/200.24 |
| D490,897 | S | 6/2004 | Ruch |
| 6,768,039 | B1 | 7/2004 | Beaudry |
| 6,769,428 | B2 | 8/2004 | Cronk et al. |
| 6,769,429 | B1 | 8/2004 | Benetti |
| 6,822,133 | B2 * | 11/2004 | Lebner ............................ 602/54 |
| 6,860,263 | B1 | 3/2005 | Scoggins |
| 6,971,388 | B1 | 12/2005 | Michaels |
| 6,978,781 | B1 | 12/2005 | Jordan |
| 6,982,359 | B1 | 1/2006 | Beaudry |
| 7,013,889 | B2 * | 3/2006 | Cronk et al. .............. 128/200.24 |
| 2001/0023695 | A1 | 9/2001 | Auriemma |
| 2001/0032645 | A1 | 10/2001 | Cronk et al. |
| 2002/0000227 | A1 | 1/2002 | Duyke et al. |
| 2003/0000521 | A1 | 1/2003 | Beaudry |
| 2003/0005938 | A1 | 1/2003 | Lockwood |
| 2003/0089375 | A1 | 5/2003 | Stratton |
| 2003/0144684 | A1 | 7/2003 | Ogle |
| 2003/0181941 | A1 | 9/2003 | Bruggisser et al. |
| 2004/0059368 | A1 | 3/2004 | Maryanka |
| 2004/0111109 | A1 | 6/2004 | Ruiz |
| 2004/0147954 | A1 | 7/2004 | Wood |
| 2004/0153019 | A1 | 8/2004 | Beaudry |
| 2004/0237967 | A1 | 12/2004 | Davis |
| 2004/0261791 | A1 | 12/2004 | Horian |
| 2005/0027230 | A1 | 2/2005 | Beaudry |
| 2005/0066965 | A1 | 3/2005 | Cronk et al. |
| 2005/0081857 | A1 | 4/2005 | Fenton |
| 2005/0124926 | A1 | 6/2005 | Beaudry |
| 2005/0131329 | A1 | 6/2005 | Beaudry |
| 2005/0247317 | A1 | 11/2005 | Lockwood, Jr. |
| 2006/0000472 | A1 | 1/2006 | Fenton |

FOREIGN PATENT DOCUMENTS

| | | |
|---|---|---|
| EP | 0 842 646 | 10/1997 |
| EP | 0 855 175 | 1/1998 |
| EP | 0 941 723 | 12/1998 |

* cited by examiner

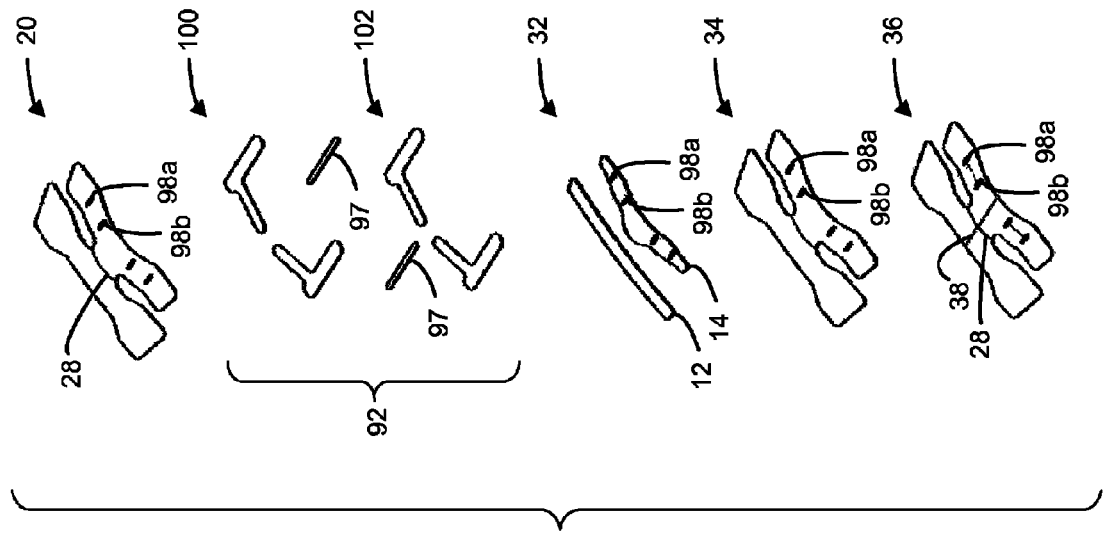
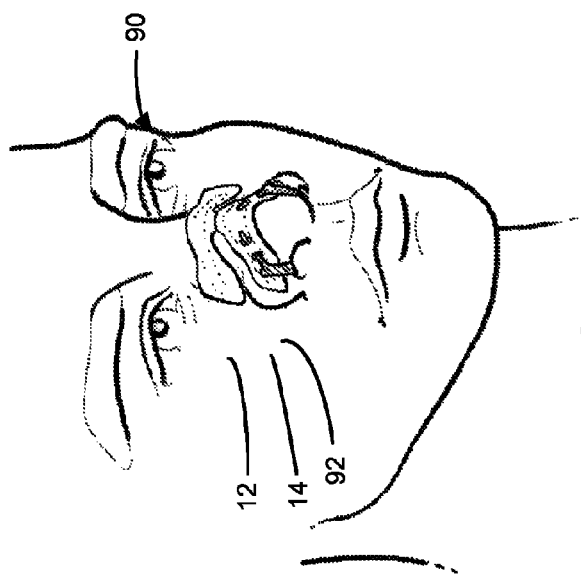
FIG. 9
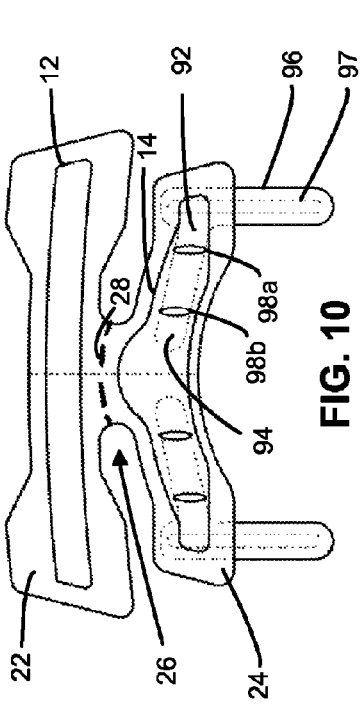
FIG. 10
FIG. 11

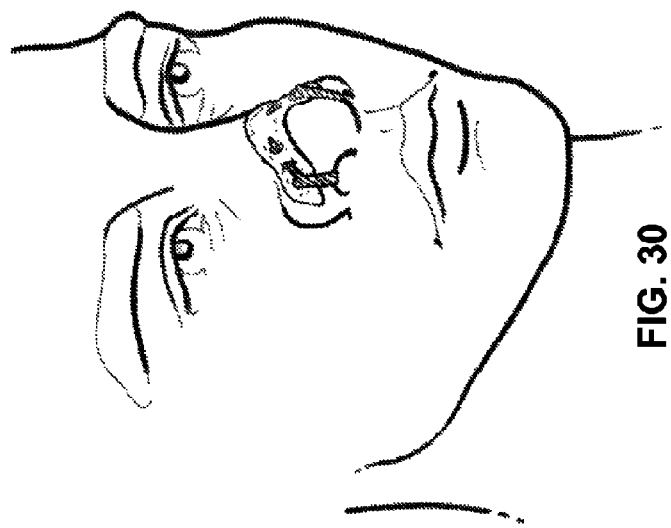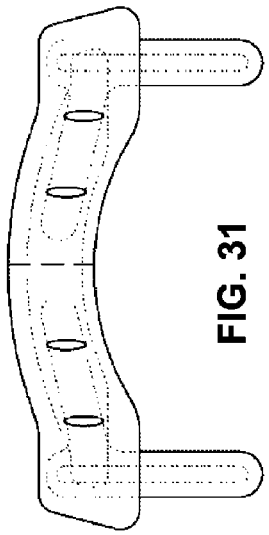
FIG. 30
FIG. 31
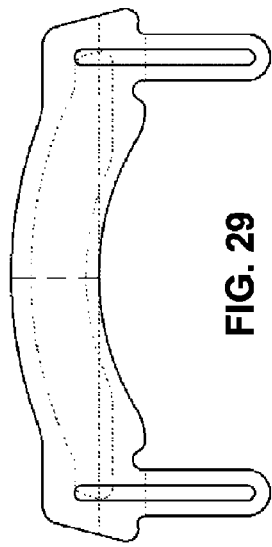
FIG. 28
FIG. 29

NASAL DILATOR

TECHNICAL FIELD

The present invention generally relates to tissue dilators and in particular to a nasal dilator.

BACKGROUND OF THE INVENTION

In order to breathe, air may be drawn into the lungs through the nasal passageway, which includes the nostrils and the nasal valve (sometimes referred to as an internal valve). Resistance within the nasal passage may make it difficult or uncomfortable to breathe or necessary to breathe through the mouth. This discomfort and/or resistance to breathing may lead to snoring, among other things. It is well understood that breathing through the nasal passages is much healthier than through the mouth due a series of physiological mechanisms in the nasal passages that help to condition the air prior to it reaching the lungs. These include, among other things, filtering, warming, moisturizing, and dehumidifying the inhaled air prior to being received by the lungs.

The nasal passageway has at least two potential areas of resistance, the internal nasal valve and the nostrils. The nasal valve is a small, slit-shape space, which is approximately 0.10 inch wide and located near the back of the nasal passageway, between the cartilage within the side wall of the nose and a partition inside the nose called the middle turbinate and septum. The nasal valve is surrounded by blood vessels, which can easily swell and block the nasal passageway, making breathing more difficult. In fact, the blood vessels surrounding the nasal valve are so easily swelled that exercise, the common cold, lying down, or pregnancy can cause enough swelling to increase nasal passage resistance and/or block the nasal passage.

The nostrils may be another source of nasal resistance, which may also be referred to as external valves. The blood vessels in the nostrils also may swell during times of exercise or when a person is lying down. The swelling causes a reduction in the cross-sectional area of the nasal passage and may make it more difficult for a person to breathe. Further, the nostrils may collapse during breathing, especially during times of heavy breathing, which is common during exercise. The collapse of the nostrils may also be caused by a nasal anatomical abnormality, such as a deviated septum which causes an uneven flow of air through the nostrils. When the outer wall of the nostril collapses the area through which the air is drawn is reduced, which may make it more difficult and/or uncomfortable to breathe.

Most conventional nasal dilators are externally mounted to the nose to dilate the tissue of the nose, but are configured such that sub-optimum nasal dilation is achieved since they are able to dilate the internal valves and have no effect on dilating the nostrils or reducing nostril collapse. Other nasal dilators, or more accurately, internal nostril supports may be mounted inside of the nostrils to dilate the nostrils and/or prevent nostril collapse. While these internal devices may be effective at reducing nostril collapse or dilating the nostrils, they are incapable of dilating both of the internal nasal valves and the nostrils.

SUMMARY

A nasal dilator for temporary attachment to a nose of a person includes an upper elongate resilient member, a lower elongate resilient member separate from the upper resilient member, and a flexible substrate for holding the upper resilient member and lower resilient member with respect to each other such that the upper resilient member acts upon the nose independently of the lower resilient member, the substrate having an upper portion secured to the upper resilient member and a lower portion secured to the lower resilient member, the upper resilient member and the lower resilient member each longer than a portion of the substrate connecting the upper and lower portions.

In one embodiment, when the nasal dilator is attached to the nose, the upper resilient member dilates the nasal valve.

In another embodiment, when the nasal dilator is attached to the nose, the lower resilient member dilates the nostrils.

In still another embodiment, the nasal dilator for temporary attachment to a nose of a person includes an adhesive bridge for spanning transversely across a mid-line of the nose and a pair of downwardly extending bendable hooks connected to the adhesive bridge and insertable into each nostril for reducing nostril collapse.

In another embodiment, the nasal dilator for attachment to a nose of a person includes an adhesive bridge for spanning transversely across a mid-line of the nose and a pair of downwardly extending tabs connected to the adhesive bridge, the tabs having an adhesive on a back surface of the tabs and for respective engagement to the sides of the nasal vestibule immediately adjacent the nostril opening.

To the accomplishment of the foregoing and related ends, certain features described hereinafter are particularly pointed out in the claims. The following description and the annexed drawings set forth in detail certain illustrative embodiments. These embodiments, however, are merely indicative of a few of the various ways in which inventive features may be employed. Other objects, advantages and novel features will become apparent from the following detailed description when considered in conjunction with the drawings.

Although the drawings and description are directed to one or more embodiments, equivalents and modifications will occur to others skilled in the art upon the reading and understanding of the specification.

Features that are described and/or illustrated with respect to one embodiment may be used in the same way, or in a similar way, in one or more other embodiments and/or in combination with, or instead of, the features of the other embodiments.

BRIEF DESCRIPTION OF THE DRAWINGS

In the accompanying drawings:

FIG. 9 is an environmental view of another embodiment of a dual truss nasal dilator that includes configurable hooks.

FIG. 10 is a top view of one embodiment of the dual truss nasal dilator of FIG. 9.

FIG. 11 is an exploded view of one embodiment of a dual truss nasal dilator of FIG. 9.

FIG. 28 is an example of a nasal dilator with a resilient member and hooks.

FIG. 29 is a top view of the nasal dilator of FIG. 28.

FIG. 30 is an example of a nasal dilator with a resilient member and configurable hooks.

FIG. 31 is a top view of the nasal dilator of FIG. 30.

DETAILED DESCRIPTION OF THE INVENTION

Figure 1:
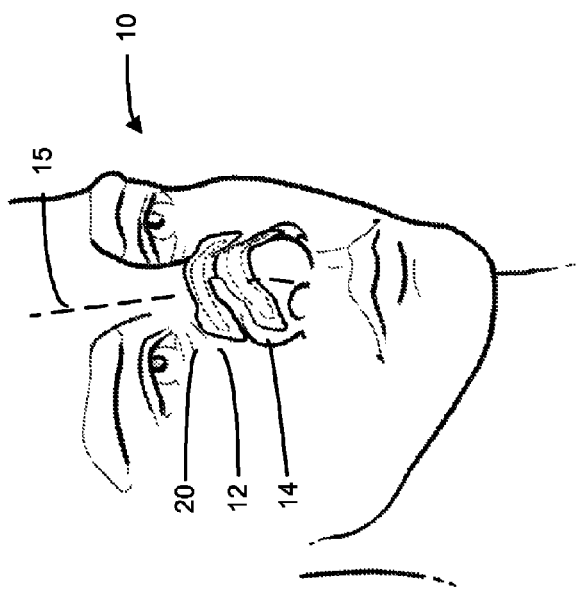
FIG. 1 is an environmental view of one embodiment of a dual truss nasal dilator for temporary attachment to a nose.

Referring to the drawings, wherein like reference numbers designate like parts in the several figures, and initially to FIG. 1, one embodiment of a dual truss nasal dilator 10 is shown. The nasal dilator 10 may be attached temporarily to the nose of a person, as shown in FIG. 1.

The nasal dilator 10 has two separate resilient members 12, 14 that extend transversely (e.g., laterally or horizontally) across a mid-line portion 15 of the nose to dilate the nasal valve and the nostrils, respectively. As shown, the upper resilient member 12 extends transversely across an upper portion of the nose, which may include the bony region of the nose. The upper resilient member 12, for example, may be attached temporarily, via the substrate 20, an adhesive, or an adhesive layer, to the skin below the eye orbital, on the cheek, on the sides of the nose, etc.

The lower resilient member 14 extends across a mid-line portion 15 of the nose below the upper resilient member 12, such as, for example, across the nasal vestibule. Like the upper resilient member 12, the lower resilient member 14 may be attached temporarily, via a substrate, an adhesive, or an adhesive layer, etc., to the skin on the sides of the nose or the nasal vestibule, or the sides of the nostrils, etc.

Each resilient member may have a naturally curved shape, to facilitate and/or enhance dilation of the nasal valve and/or nostrils. When the resilient members are not acting on the nose, the lateral ends of each of the resilient members may curve away from the nose and face. For example, the resilient members may be curved such that the surface of the resilient members 12, 14 proximal the user, e.g., the user-side surfaces, forms generally convex surfaces before the nasal dilator is attached to the nose, and the surface of the resilient members distal the user form concave surfaces. In one embodiment, the curvature of the nasal dilator has approximately a 3 inch radius.

The curvature, or pre-bias, of the resilient members also bend the substrate 20 and any adhesive layers, as described below, so that the user-side of the nasal dilator 10 is curved away from the nose and face of the user. It will be appreciated that initially flat and oppositely curved resilient members also may be used to dilate the nasal valve and/or nostrils.

The attachment of the nasal dilator 10 to the skin, in part with a spring like force from the resilient members, tends to dilate the nasal passage by gently lifting or pulling the skin away from the face. The pulling of the skin, even a slight distance away from the face, tends to cause the nasal valve and nostrils to dilate and relieve resistance in the nasal passageway.

When the upper resilient member 12 acts on the nose, at or near the bony region, and in conjunction with adhesive on the substrate 20 or adhesive directly on the upper resilient member 12 and/or the resiliency or pre-bias of the resilient members, the nasal valve tends to be dilated, thereby relieving or reducing resistance in the nasal passage.

The lower resilient member 14 dilates the nostrils in a similar manner. The lower resilient member extends across the mid-line portion 15 of the nose, below the upper resilient member 12, e.g., across the nasal vestibule, and is attached temporarily to the skin at or around the nasal vestibule on the sides of the nose. The lower resilient member 14, in conjunction with adhesive and/or the resiliency of the resilient member 14 tends to expand or dilate the nostrils and thereby decrease or reduce resistance in the nasal passage. If a portion of the lower resilient member 14 is attached to the sides of the nostrils, the lower resilient member 14 also tends to reduce or diminish nostril collapse. In this manner, the resilient member will act as a reinforcing support to the outer wall of the nostrils. In reinforcing the outer wall of the nostril, the nostril is less likely to collapse under normal breathing conditions, and it will require a greater force to collapse the nostril.

Figure 2:
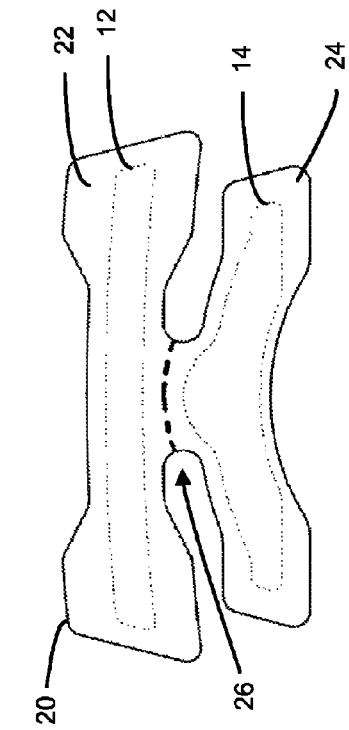
FIG. 2 is a top view of one embodiment of the dual truss nasal dilator of FIG. 1.

Referring now to FIG. 2, the dual truss nasal dilator 10 of FIG. 1 is depicted in greater detail. The nasal dilator 10 is includes the substrate 20 and upper and lower resilient members 12, 14, respectively. The substrate 20 may include one or more layers cut from webs of material.

When the nasal dilator 10 is attached temporarily to the nose, the upper resilient member 12 extends transversely across the bony portion of the nose to dilate the nasal valve in each nostril, as shown in FIG. 1. The upper resilient member 12 may be elongate in shape and may be long enough in length to span across the bony region of the nose and to act on the nose to dilate the nasal valve. The upper resilient member 12 also may be long enough in length to interact with the skin, either on the sides of the bony region of the nose or at areas around the cheek areas or where the cheeks meet the side of the nose. The upper resilient member 12 may be an elongate, slightly curved rectangle, as shown in FIG. 2, or any other elongate shape, such as a rectangle, arch or oval, etc., as will be appreciated by one of skill in the art. In one embodiment, the upper resilient member is about 1.75 inches to about 2.75 inches long.

The lower resilient member 14 also may be elongate in shape and long enough in length to span across at least a portion of the nasal vestibule to dilate the nostrils by engaging the outer skin of the nostrils below the bony region of the nose. In the embodiment of FIG. 2, the lower resilient member 14 is an arch shape, having a middle portion extending generally along the mid-line portion 15 of the nose and toward the upper resilient member 12 to provide support, rigidity and increased resiliency to the lower resilient member 14. Alternatively, the lower resilient member 14 may be substantially the same shape as the upper resilient member 12, e.g., an elongate, slightly curved rectangular shape, arch, oval, etc., as will be appreciated by one of skill in the art. In one embodiment, the lower resilient member 14 is about 1.5 inches to about 2.75 inches long and is shorter than the upper resilient member 12 by about 0.25 inches to about 1.0 inches.

The upper and lower resilient members 12, 14 are held with respect to each other by the substrate 20 such that the upper resilient member 12 acts on the nose independently of the lower resilient member 14. The substrate 20 may be attached or secured to the resilient members by an adhesive. In one embodiment, the resilient members are sandwiched between an outer substrate layer and an inner substrate layer.

In the embodiment depicted in FIG. 2, the substrate 20 has an upper portion 22, a lower portion 24, and a portion 26 connecting the upper portion 22 to the lower portion 24. The substrate 20 may follow the contours of the resilient members such that the upper portion 22 and the lower portion 24 are wider than the portion 26 connecting the upper and lower portions. The length of the portion 26 connecting the upper portion 22 and lower portion 24 is long enough to span across the mid-line portion 15 of the nose, but may be shorter than the length of the resilient members 12, 14 such that the nasal dilator has an overall butterfly shape.

The length of the portion 26 along with the flexibility of the substrate 20, among other things, allow the upper resilient member 12 and lower resilient member 14 to act independently of one another on the nose. The upper resilient member 12 may act on an upper portion of the nose to dilate the nasal valve independently of the lower resilient member 14, which can act on the nasal vestibule to dilate the nostrils. The portion 26 connecting the upper portion 22 to the lower portion 24 also may have a length that is long enough the span across the mid-line portion 15 of the nose without extending substantially onto or past the sides of the nose. In one embodiment, the portion 26 is about 0.75 inches long.

In another embodiment, the substrate may resemble a vertical strip that extends generally along the mid-line portion 15 of the nose, from an upper part of the nose, e.g. near the bridge of the nose, to the tip of the nose. The upper portion 22 of the substrate 20 and the lower portion 24 of the substrate 20 may be attached to the upper resilient member 12 and lower resilient member 14, respectively, to hold the resilient members with respect to each other. The resilient members 12, 14 may extend laterally or transversely across the mid-line portion 15 of the nose to dilate the nasal valve and/or nostrils, and may be longer than corresponding securing portions of the substrate 20.

Figure 3:
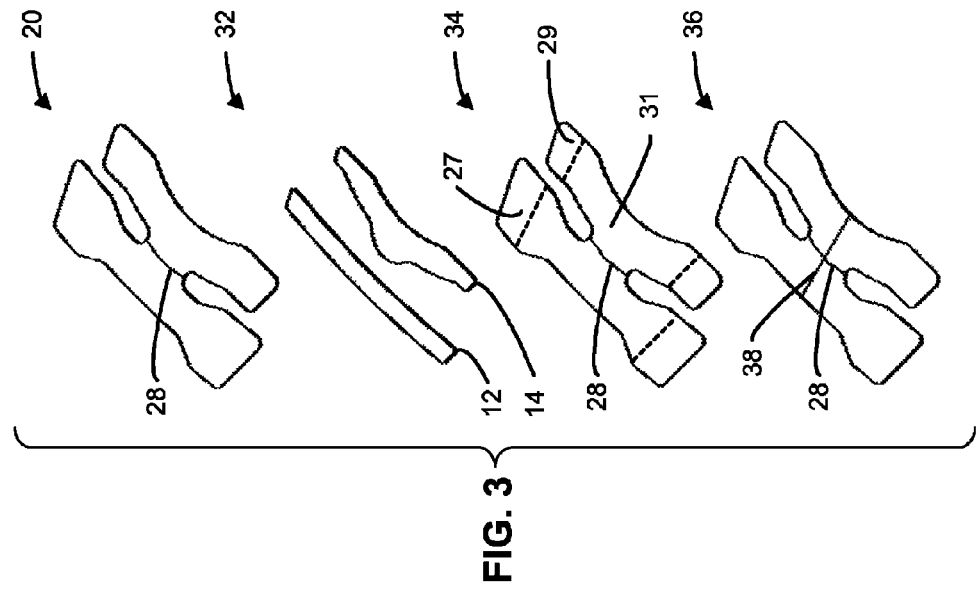
FIG. 3 is an exploded view of the dual truss nasal dilator of FIG. 1.

The user-side of the upper and lower resilient members 12, 14 may have an adhesive to attach the resilient members temporarily to the nose. The adhesive may be located on the lateral ends of each resilient member such that the ends of the resilient members 12, 14 are attached to the nose while the portions of the resilient members along the mid-line portion 15 of the nose are not attached to the nose. The adhesive also may be applied to or cooperative with the substrate 20. The adhesive may be applied across the entire user-side surface of the substrate 20, or may be applied to a portion of the surface. For example, the adhesive may be adjacent the lateral ends of the upper and lower portions 22, 24 of the substrate 20, e.g., the portions that attach to the sides of the nose 27 or sides of the nasal vestibule 29, but not across the portion 31 that spans the mid-line portion of the nose 15, as shown in FIG. 3. It will be appreciated that these and other embodiments of the adhesive layer may be applied to any of the embodiments of the nasal dilator described herein.

Regardless of the exact shape, the substrate 20 holds the upper and lower resilient members with respect to each other. The substrate 20 may hold the resilient members such that they are spaced from one another, as depicted in FIG. 2. It will be appreciated however, that the substrate may hold the resilient members 12, 14 in other configurations as well, such as, for example, overlapping one another. It will be appreciated, however, that even if the resilient members overlap one another, they still may act on the nose independently of one another to dilate the nasal valve and/or nostrils.

In some cases, it may be desirable to use the upper resilient member 12 or the lower resilient member 14 separately from one another. For example, a user may desire to dilate only the nasal valve and not the nostrils, or vice versa. Alternatively, a user may desire to space the upper resilient member 12 and lower resilient member 14 from one another for placement on the nose at a greater or smaller distance than spacing of the resilient members when held by the substrate 20. Such spacing may be used to achieve different dilation results, for increased comfort, or to accommodate longer or shorter noses. In order to allow the user to use the nasal dilator 10 in these or similar manners, the portion 26 of the substrate connecting the upper portion 22 and lower portion 24 may be frangible or separable along a separating line 28. For instance, the upper and lower portions 22, 24 may be made separable by including perforations in the substrate 20 (in which case the separating line 28 is defined by the perforations), by scoring the substrate, and so forth. The mechanical weakness of the substrate 20 at the separating line 28 may allow the upper portion 22 to be separated easily from the lower portion 24 by tearing, breaking, or otherwise separating the substrate at the separating line 28.

Alternatively, the nasal dilator 10 may have a single lower resilient member 14, substantially the same as that described herein for dilating the nostrils and/or or for preventing nostril collapse, as will be described in more detail below. In another alternative, the dilator 10 may have a single upper resilient member 12 or adhesive bridge for attaching the nasal dilator temporarily across an upper portion of the nose to dilate the nasal valve, as described herein and as will be described in more detail below.

Referring now to FIG. 3, an exploded view of the dual truss dilator 10 is shown and illustrates the construction of the nasal dilator 10 depicted in FIG. 1. As shown, the nasal dilator 10 may have a multi-layer construction, including a substrate 20, a resilient member layer 32, an adhesive layer 34, and a release film 36.

The substrate 20 may be may be made from a flexible material (e.g., a plastic or polymeric material) or fabric and may include one or more sub-layers. The substrate 20 may be porous and/or hypoallergenic. The thickness or shape of the substrate layer may be varied to achieve desired performance, cost, look, feel, and ease of use. The substrate 20 may have adhesive on one side for holding the resilient members 12, 14 with respect to each other and/or for attaching the nasal dilator 10 to the nose.

In an exemplary embodiment, the substrate 20 may be about 0.006 inches thick and constructed from a perforated polyethylene film, having a pressure sensitive adhesive on one side. One such suitable material is 3M Transpore® tape, which is a porous, hypoallergenic tape made from an organic polymer. It will be appreciated by one of skill in the art, however, that other materials may be suitable for the substrate 20. Such materials include, but are not limited to, various polymers, soft PVC, polyurethane, polypropylene, woven fabric and the like.

The nasal dilator 10 also includes the resilient member layer 32, which includes the resilient members 12, 14. Each resilient member 12, 14 may be made from one or more sub-layers. The resilient members 12, 14 are preferably constructed from a thin, flexible material that has enough resiliency to supply dilating force to the nasal valve and/or nostrils, and/or to reinforce the nostrils to reduce nostril collapse. The relative rigidity and flexibility of the material may be considered, and different materials may be used for the resilient members depending on the desired performance, cost, look, feel and ease of use. The upper resilient member 12 and the lower resilient member 14 may be constructed from different materials and/or have different resiliencies, to achieve different dilation results on the nasal valve and nostrils. For example, it may be desirable to use a material with a greater resiliency to dilate the nasal valve and a lower resiliency to dilate the nostrils, or vice versa. The performance of the material may be affected by, among other factors, the material thickness, the shape of the resilient member, the cross-sectional profile, the spring force, etc. Additional factors to consider when choosing a material for the resilient members include deflection of the material with increased temperature and the deformation of shape of the material under stress and/or over a specified length of time.

In one embodiment, the resilient members 12, 14 are constructed from about 0.010 inch thick polyester flat stock with a spring force rating of about 25 grams to about 28 grams when applied to skin. Additional materials may also be suitable for the resilient members, as will be appreciated by one of skill in the art. For example, other suitable materials include, but are not limited to, various polymers, PETG, Nylon 6/12, 6/6, Acetate-CA, CAB, CAP and EC, Acrylic-Lexan™, Acetal-Delrin™, PVC, polycarbonate, PEEK, HD polyethylene, HD polypropylene, polystyrene, ABS, or any other extruded, injection molded, blown, compressed, thermoplastic, or thermoset materials. Multiple layers of the same or diverse materials may be used to construct the resilient members 12, 14.

The adhesive layer 34 may include an adhesive on one or both sides of the adhesive layer, e.g., a double-sided adhesive having adhesive on the user-side and the non-user side of the layer. The adhesive layer 34 may be made from one or more sub-layers. The adhesive layer 34 may be formed from a material that is hypoallergenic and approved for skin contact for an extended period of time. Other factors to consider for the adhesive layer 34 include the adhesion strength, which generally is the force required to separate two bonded surfaces and the peel strength, which is force required to peel apart two sheets of material that have been joined with the adhesive. Adhesion and peel strengths will have a range based on the thickness of the adhesive, amount of surface area in contact with the bonding substrate and the condition of the substrate. For example, having a large adhesive contact area that is not directly affected by the spring pressure of the resilient member will increase adhesion, while a small adhesive contact area that is directly affected by the spring force of the resilient member will decrease adhesion.

Suitable materials for the adhesive layer 34 include, for example, Mactac TM9710 acrylic-based adhesive with a polyester carrier, hypoallergenic double-sided 0.0035 inch thick PSA and supplied with a 60# semi-bleached Kraft paper with silicone release on both sides and having a peel strength of 6.9 lb/in within 30 minutes and a 100% elongation. Additional materials that may be suitable for the adhesive layer 34 include: synthetic rubber based adhesives, natural rubber based adhesives, acrylate based adhesives, or acrylic based adhesives, etc.

As will be appreciated, an adhesive component of the adhesive layer 34 may form one adhesive layer 34 sub-layer, and a polymer or fabric backing may form another adhesive layer 34 sub-layer. Additional adhesive and stock material layers may be present, such as a second adhesive layer to provide "double-sided" adhesion to a backing sub-layer.

The release film 36 is paired with the adhesive layer 34 or the adhesive on the substrate 20 to protect the adhesive from damage, loss of adhesive quality or properties, and/or premature adhesion to a surface other than the user's skin. The peel strength of the adhesive layer 34 and the release film 36 may be considered when selecting an appropriate material. The release film 36 may be parted or pre-separated along a parting 38 to promote easy removal of the release of the release film 36 from the adhesive layer 34, such as, for example, is common with a bandage. The parting may be formed during construction of the nasal dilator 10 with die cut, overlapping layers or may be formed with any other known and accepted production methods, as will be appreciated by one of skill in the art.

In the illustrated embodiment, the substrate 20 has adhesive on a user-side surface. The adhesive of the substrate 20 secures the resilient members 12, 14 thereto and secures the substrate to an outside surface of a backing sub-layer of the adhesive layer 34. In this case, one could consider the substrate 20 and the backing to cooperate as a multilayer substrate in which the resilient members 12, 14 are sandwiched. In this embodiment, adhesive on a user-side of the backing secures the nasal dilator 10 to the user.

In another embodiment, the substrate has adhesive on a user-side surface. The adhesive of the substrate 20 secures the resilient members 12, 14 thereto and excess adhesive surrounding the resilient members 12, 14 is used to secure the nasal dilator to the user. In this embodiment, the adhesive layer 34 may be omitted or may be made of adhesive applied to a user-side of the resilient members 12, 14 without a secondary sub-layer.

In yet another embodiment, the substrate 20 and adhesive layer 34 may be combined to form a single substrate/adhesive layer, such that adhesive is exposed on a user-side of the substrate 20. The resilient members 12, 14 may be attached to the non-user-side of the adhesive/substrate layer via an adhesive applied to the resilient members 12, 14, or via adhesive on the non-user side of the combined substrate/adhesive layer, or via another way of attaching, as will be appreciated. The adhesive on the user-side, or bottom, of the combined substrate/adhesive layer may then be used to attach the nasal dilator temporarily to the nose.

As will be appreciated, other configurations are possible. For example, the substrate 20 may not have adhesive, the resilient members 12, 14 may have adhesive on one or both sides, the substrate 20 may be omitted in favor of a backing sub-layer of the adhesive layer 34, and/or adhesive may be applied to one or both sides of a backing sub-layer of the adhesive layer 34, to name a few other possible configurations.

Regardless of how the nasal dilator 10 is constructed and to which components adhesive is applied, one or more adhesive layers may be used to attach the nasal dilator temporarily to the nose so that the resilient members may dilate the nasal valve and/or the nostrils.

As described above, the upper portion 22 and the lower portion 24 may be separated from each other at a separating line 28. The separating line 28 may be made in each layer individually and before the layers are assembled with one another. Alternatively, even though shown in each individual layer, the separating line 28 may be made after the layers are assembled by, for example, perforating, cutting or scoring all or some of the layers of the assembled nasal dilator 10 at the same time.

Figure 4:
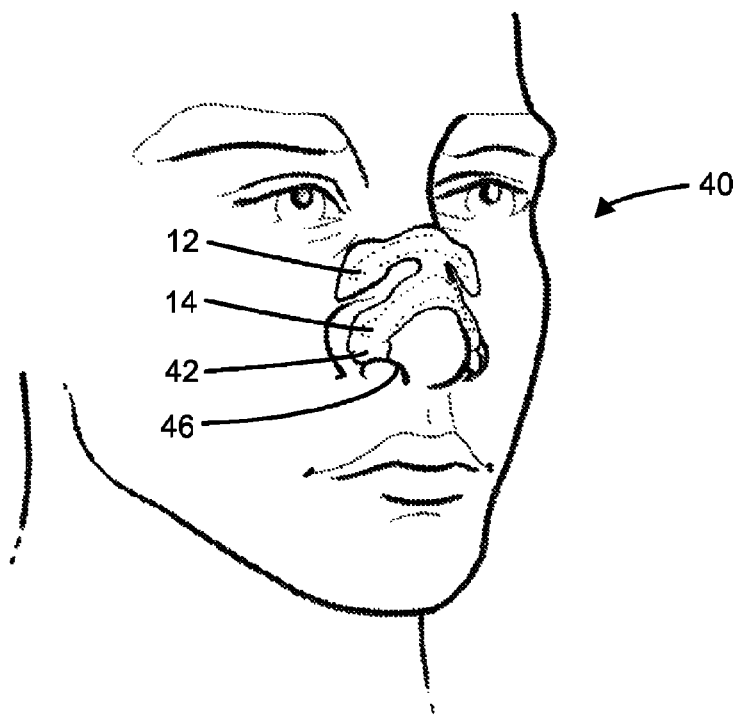
FIG. 4 is an environmental view of another embodiment of a dual truss nasal dilator that includes adhesive tabs.

Another embodiment of a dual truss nasal dilator 40 is depicted in FIG. 4. The nasal dilator 40 has an upper resilient member 12 and a lower resilient member 14 to dilate the nasal valve and the nostrils, respectively, as described with respect to FIG. 1 above. Generally, the overall construction of the nasal dilator 40 is similar to the nasal dilator 10, and includes the same or similar layers, such as the substrate 20, the resilient members 12, 14, the adhesive layer 34, and the release film 36. For sake of brevity, the similarities between the dilator 10 of FIGS. 1-3, and the dilator 40 of FIG. 4, will not be repeated.

The nasal dilator 40 further comprises adhesive tabs 42, which extend downwardly, in the general direction of the nostril openings 46. In one embodiment, the adhesive tabs 42 may be integrated with the substrate 20, such that the tabs 42 are cut at the same time and from the same webstock as the substrate 20. The user-side surface of the tabs 42 may have an adhesive for attaching the tabs 42 temporarily to the sides of the nasal vestibule to reinforce or support the nostrils and reduce or inhibit nostril collapse.

Figure 5:
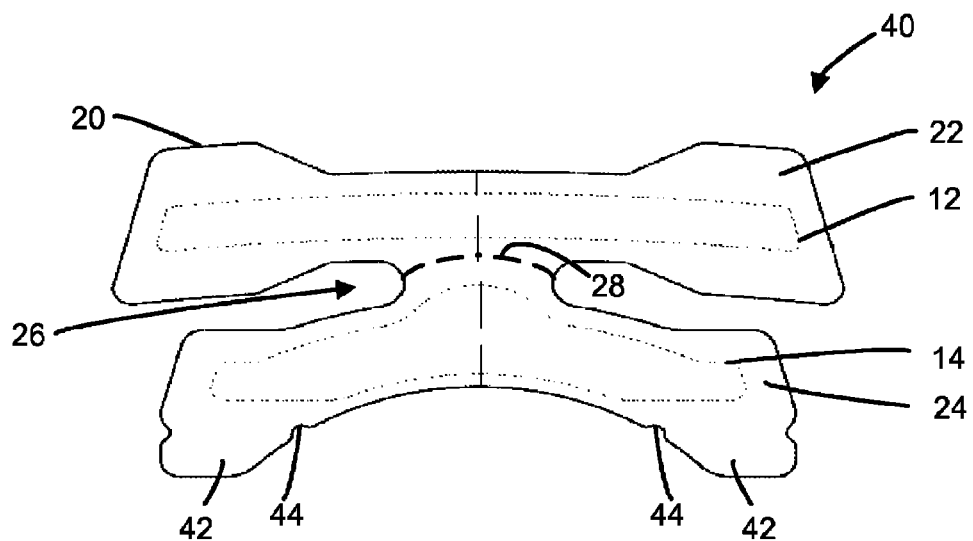
FIG. 5 is a top view of one embodiment of the dual truss nasal dilator of FIG. 4.

A top view of the nasal dilator 40 with the adhesive tabs 42 is depicted in FIG. 5. The adhesive tabs 42 may be integrated with the lower portion 24 of the substrate 20. The adhesive tabs 42 extend downwardly from the lower portion 24 of the substrate 20 in the general direction of the nostril openings. The perimeter or edges of the substrate 20 may have grooves 44 to facilitate the bending and adhesion of the adhesive tabs 42 to the outer skin of the nasal vestibule. The adhesive tabs 42 tend to reduce nostril collapse during times of heaving breathing by adding support to the outer skin of the nostril. In one embodiment, the adhesive tabs 42 extend to the edge of the nostril opening 46, as shown in FIG. 4. The adhesive on the tabs 42 may be applied directly to the substrate 20 that forms the tabs 42. Alternatively, an adhesive layer 34 may be attached to the underside or user-side of the substrate 20 or a backing layer of the adhesive layer 34, if present or used in lieu of the substrate 20.

Figure 6:
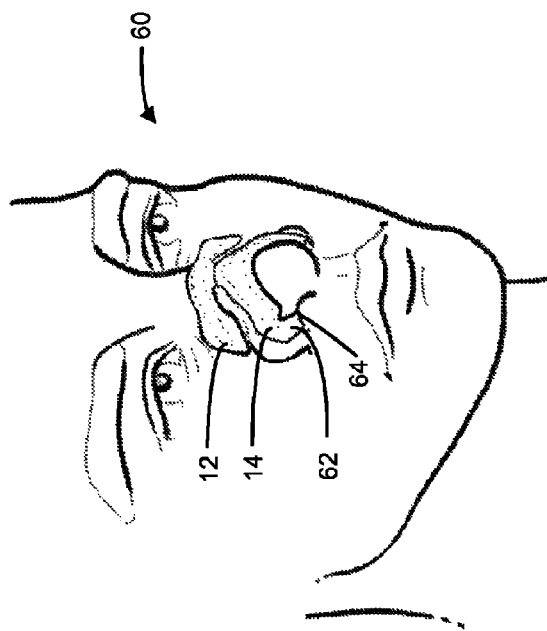
FIG. 6 is an environmental view of another embodiment of a dual truss nasal dilator that includes hooks.

FIG. 6 depicts yet another embodiment of a nasal dilator 60. The nasal dilator 60 has an upper resilient member 12 and a lower resilient member 14 to dilate the nasal valve and the nostrils, respectively, as described with respect to FIG. 1 above. Generally, the overall construction of the nasal dilator 60 is similar to the nasal dilator 10, and includes the same or similar layers, such as the substrate 20, the resilient members 12, 14, the adhesive layer 34, and the release film 36. For sake of brevity, the similarities between the dilator 10 of FIGS. 1-3, and the dilator 40 of FIG. 4, will not be repeated.

The nasal dilator 60 includes bendable hooks 62, which extend downwardly from the lower portion 24 of the substrate 20, and in the general direction of the nostril openings 64. As shown in FIG. 6, the bendable hooks 62 may be bent and inserted into the nostrils to mechanically minimize, reduce or inhibit nostril collapse. The bendable hooks 62 may be bent in a "U" or "J" configuration around the inner and outer skin that forms the nostril and may extend into the nostril opening. The hooks 62 include a support member 63 (FIG. 7) that holds the bent shape of the hook 62 so that the bendable hooks 62 support the outer wall of the nostril. In use, the nasal dilator 60 may be secured to the nose with adhesive and the hooks 62 may be bent by the user in to the nostrils.

Figure 8:
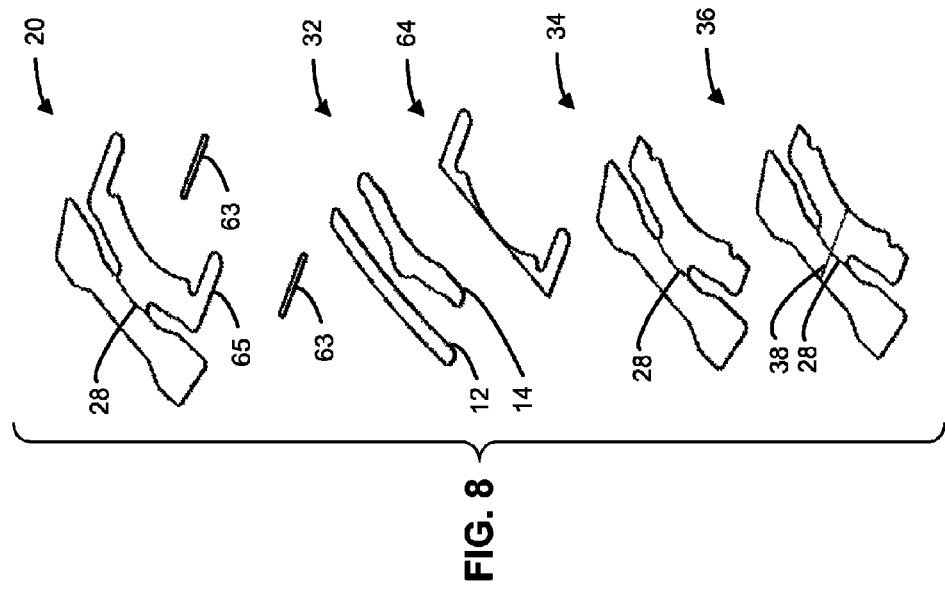
FIG. 8 is an exploded view of one embodiment of a dual truss nasal dilator of FIG. 6.
Figure 7:
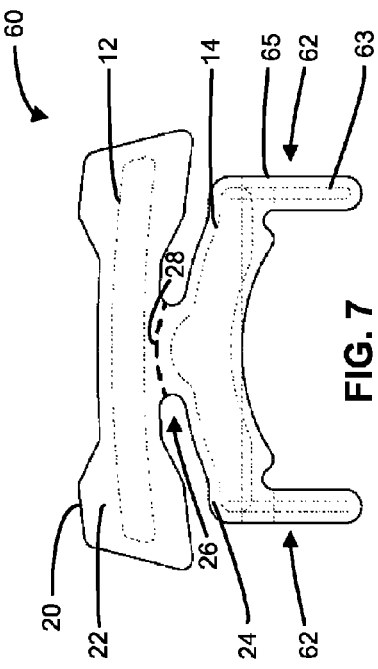
FIG. 7 is a top view of one embodiment of the dual truss nasal dilator of FIG. 6.
Figure 12:
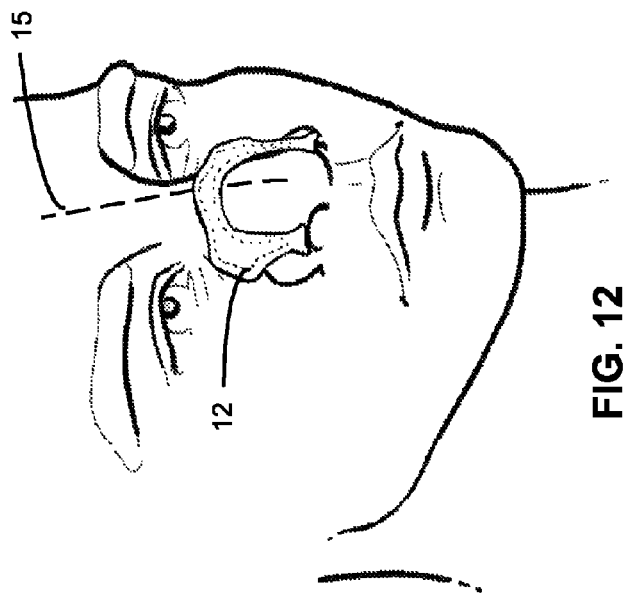
FIG. 12 is an example of a nasal dilator with a single truss and adhesive tabs.
Figure 13:
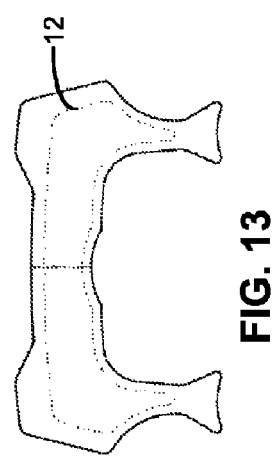
FIG. 13 is a top view of the nasal dilator of FIG. 12.
Figure 14:
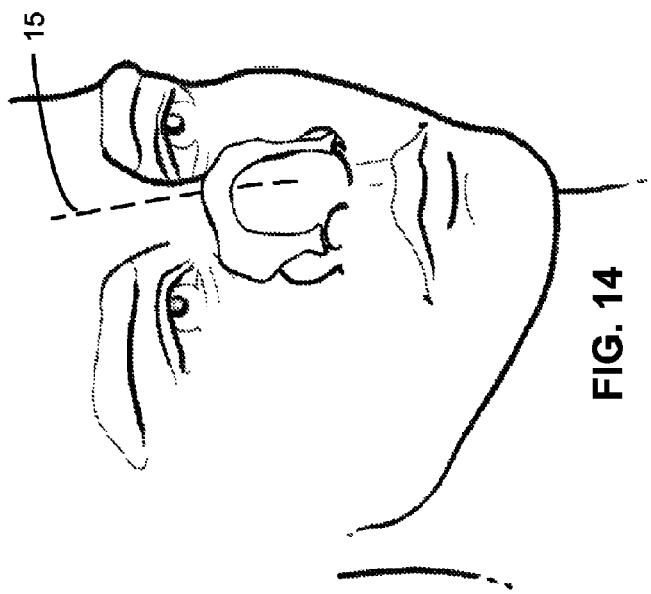
FIG. 14 is an example of a nasal dilator with an adhesive bridge and adhesive tabs.
Figure 15:
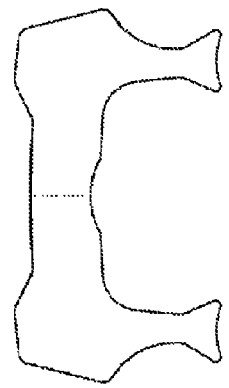
FIG. 15 is a top view of the nasal dilator of FIG. 14.
Figure 18:
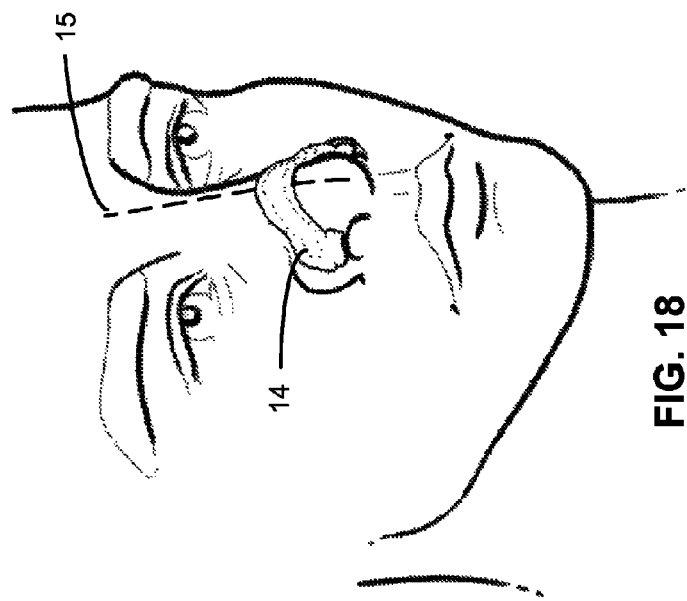
FIG. 18 is an example of a nasal dilator with a resilient member and adhesive tabs.
Figure 19:
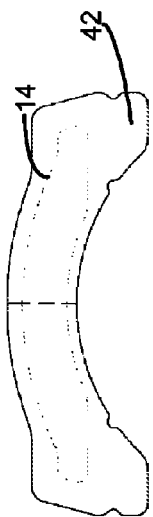
FIG. 19 is a top view of the nasal dilator of FIG. 18.
Figure 16:
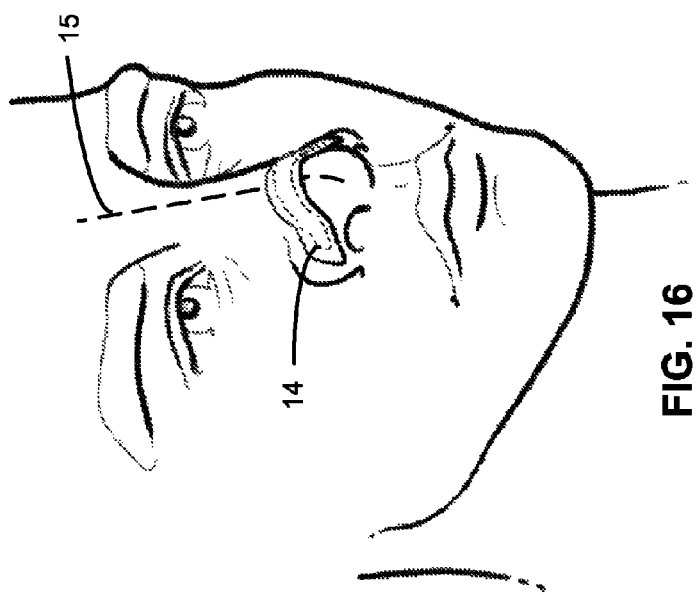
FIG. 16 is an example of a nasal dilator with a resilient member.
Figure 17:
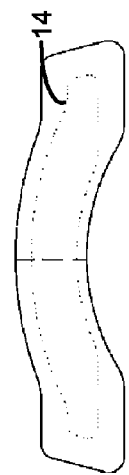
FIG. 17 is a top view of the nasal dilator of FIG. 16.
Figure 20:
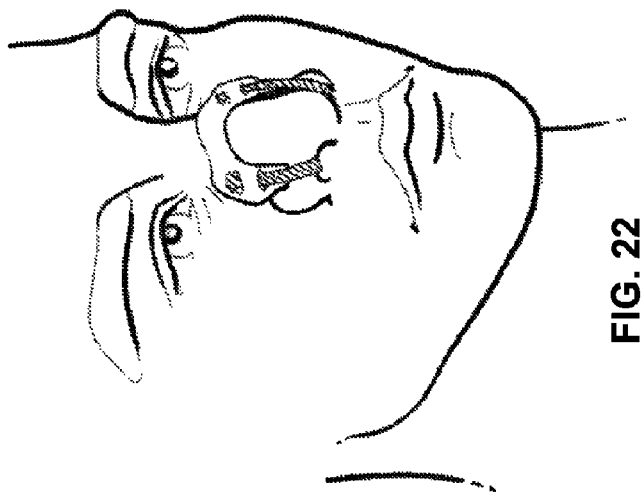
FIG. 20 is an example of a nasal dilator with an adhesive bridge and hooks.
Figure 21:
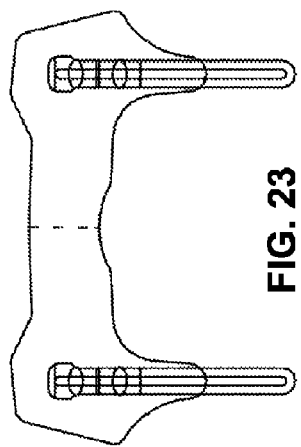
FIG. 21 is a top view of the nasal dilator of FIG. 20.
Figure 22:
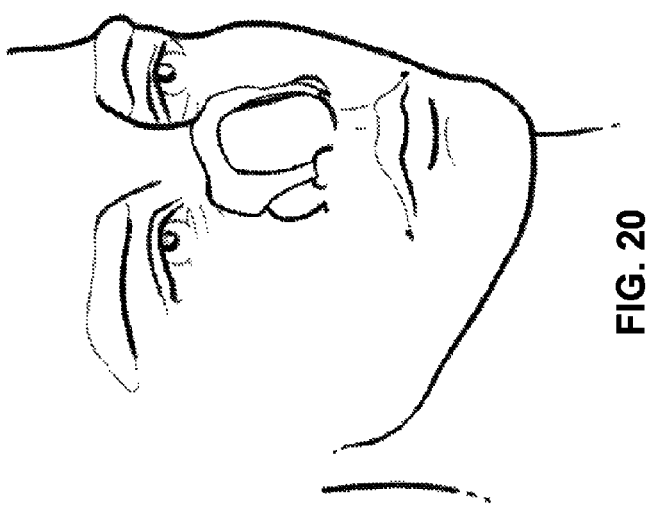
FIG. 22 is an example of a nasal dilator with an adhesive bridge and configurable hooks.
Figure 23:
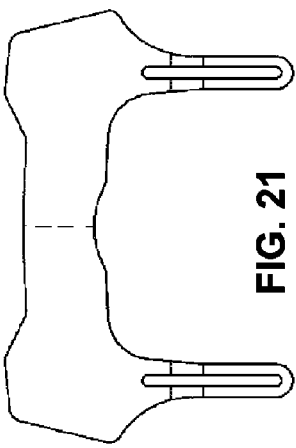
FIG. 23 is a top view of the nasal dilator of FIG. 22.
Figure 24:
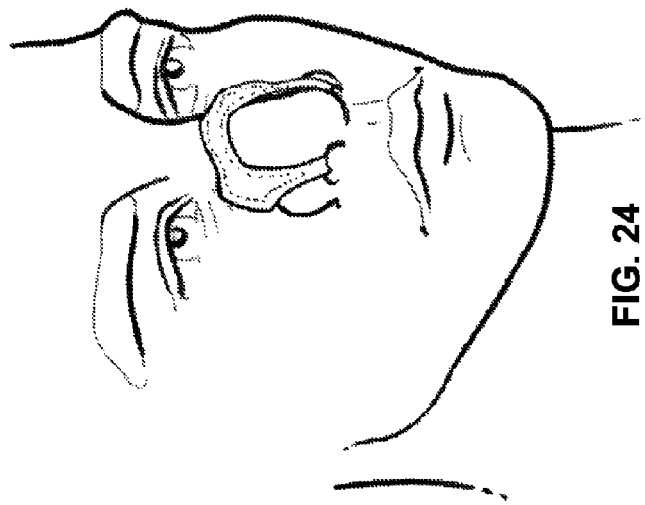
FIG. 24 is an example of a nasal dilator with a resilient member and hooks.
Figure 25:
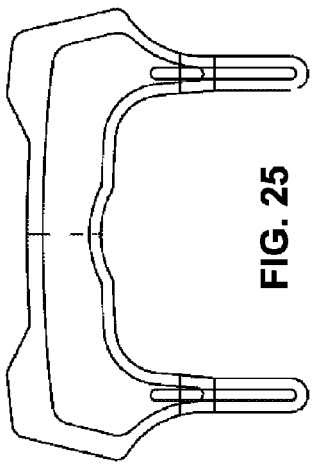
FIG. 25 is a top view of the nasal dilator of FIG. 24.
Figure 26:
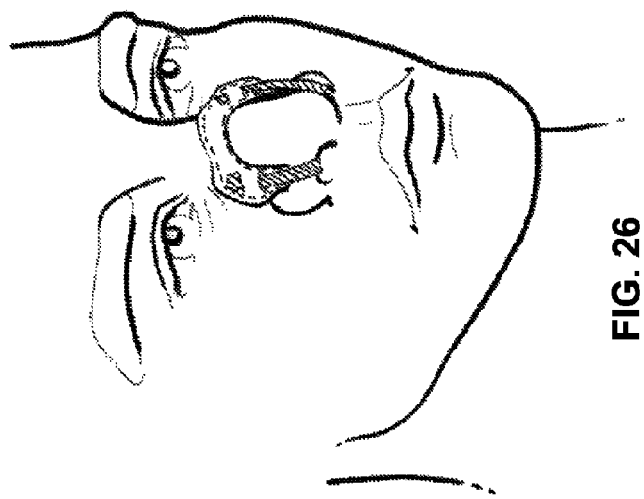
FIG. 26 is an example of a nasal dilator with a resilient member and configurable hooks.
Figure 27:
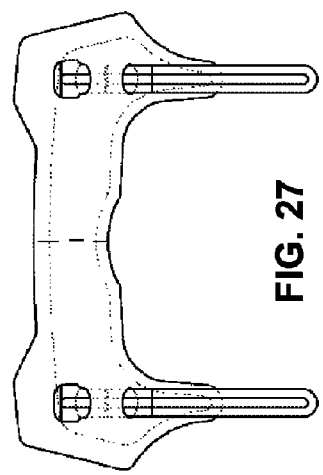
FIG. 27 is a top view of the nasal dilator of FIG. 26.

The embodiment of the nasal dilator 60 of FIG. 6 is depicted in greater detail in FIGS. 7 and 8. The bendable hooks 62 extend in a generally perpendicular direction downwardly from the lower portion 24 of the substrate 20 and the lower resilient member 14. The bendable hooks 62 may include thin, elongate support members 63, which are retained by corresponding fingers 65 of the substrate and/or a hook substrate layer 64. With the exception of the bendable hooks 62 and the hook substrate layer 64, various layers of the nasal dilator 60 have been described in detail with respect to FIG. 3, and for brevity will not be repeated here.

The support member 63 may be constructed from materials having a wide variety of different gauges and shapes. The materials may be selected to achieve any desired or required performance, cost, look, feel and easy of use, etc. Suitable metal materials may include, but are no limited to, stainless steel, copper, aluminum, or any other metal or known alloy, etc. Other suitable materials may include non-metal materials, such as, for example, polypropylene, HDPE, acetal, polycarbonate, nylon, polyester, or any other extruded, injection molded, blown, compressed thermoplastic or thermoset materials. If a non-metal material is used, it may be preferable to die cut bend points in the bendable hook 62 so that the hook retains a bent shape to support the nostril wall and mechanically counter or reduce nostril collapse. In another embodiment, the hooks 62 may be pre-bent and/or may permanently form a hook shape. In this embodiment the hooks 62 may be inserted into the nostrils and then the rest of the nasal dilator 60 may be secured to the nose with adhesive.

Below the support member 63 and corresponding fingers 65 of the substrate is the hook substrate layer 64. The hook substrate layer 64, in conjunction with the substrate 20, retains the support members 63 in a relatively fixed position with respect to the rest of the nasal dilator 60 by sandwiching the support member 63 between the two layers (the substrate 20 and the hook substrate layer 64). As describe above, one side of the substrate 20 may have a pressure sensitive adhesive, which may be pressed against the hook substrate layer 64 to secure the support members 63 to the rest of the nasal dilator 60 in a relatively fixed orientation. The hook substrate layer 64 also may have a pressure sensitive adhesive on the surface that contacts the support member 63. The bottom or user-side of the hook substrate layer 64, which contacts the skin on the inside of the nostril when the hooks 62 are inserted into the nostril, is preferably free from adhesive. The portion of the hook substrate layer 64 that is not inserted into the nose and does not contact the inner skin of the nostril, however, may have an adhesive, which allows the hook 62 to further counter or reduce nostril collapse. In other words, the user-side of the hook 62 may have an adhesive portion and a non-adhesive portion. The adhesive portion may adhere to the outer skin of the nostril to reduce or minimize nostril collapse, while the non-adhesive portion may be inserted and bent in the nostril to reduce or inhibit nostril collapse.

FIG. 9 depicts yet another embodiment of a nasal dilator 90. The nasal dilator 90 has an upper resilient member 12 and a lower resilient member 14 to dilate the nasal valve and the nostrils, respectively, as described with respect to FIG. 1 above. Generally, the overall construction of the nasal dilator 90 is similar to the nasal dilator 10, and includes the same or similar layers, such as the substrate 20, the resilient members 12, 14, the adhesive layer 34, and the release film 36. For sake of brevity, the similarities between the dilator 10 of FIGS. 1-3, and the dilator 90 of FIG. 9, will not be repeated.

The nasal dilator 90 has configurable hooks 92, which may be bent and inserted into the nostrils to mechanically reduce or inhibit nostril collapse, as shown in FIG. 9. The configurable hooks 92 allow the user to use the hooks 92 as described above, for example with respect to FIG. 6, or, if the user desires, the hooks 92 may be removed and the nasal dilator 90 may be used, for example, as described with respect to FIG. 1. For example, the user may want to use the configurable hooks 92 to help prevent nostril collapse during times of heavy exercise or heavy breathing, but prefer not to use the hooks while sleeping, or vice versa. The configurable hooks 92 offer the user the option to use the hooks 92 when desired and to remove the hooks 92 when they are not desired. The configurable hooks 92 also may allow the user to adjust, manipulate, or move the hooks 92 to increase or maximize comfort and/or effectiveness.

The nasal dilator 90 with configurable hooks 92 is depicted in greater detail in FIGS. 10 and 11. The configurable hooks 92 may have a generally "L" shape, having an arm portion 94 and a leg portion 96. The leg portion 96 may have bendable support members 97, similar to the support members 63, described above, to allow the user to insert and bend the leg portion 96 into the nostril to mechanically reduce or inhibit nostril collapse.

Slots 98*a*, 98*b* may be provided in the layers of the nasal dilator 90 and in particular the substrate 20, any backing sub-layer of the adhesive layer and the lower resilient member 14. The slots 98*a*, 98*b* may be sufficiently wide to accommodate the arm portion 94 of the configurable hooks 92, but narrow enough to hold the configurable hook 92 in a relatively fixed position. The slots 98*a*, 98*b* also allow the user to move or slide the configurable hooks 92 with respect to the nose so that the user can increase or maximize comfort and/or nostril support.

The arm portion 94 may be attached to the nasal dilator 90 as shown in FIGS. 9 and 10. The arm portion 94 may be inserted into a first slot 98*a* and beneath a portion of the substrate 20 between the slots 98*a* and 98*b*, and protrude back through the second slot 98*b*, being held relatively securely in place under the substrate 20. The bottom or user-side of the substrate 20 between the slots 98*a*, 98*b*, may be substantially flexible enough and relatively adhesive free to allow the arm portion 94 to slide beneath the substrate 20 with relative ease. Alternatively, the arm portion 94 may be inserted through notches 98*a*, 98*b* in both the substrate 20 and the lower resilient member 14, in substantially the same manner, such that the lower resilient member 14 and substrate 20 hold the arm portion 94, and therefore the configurable hook 92 relatively in place.

As shown in FIG. 11, the configurable hooks 92 may be formed independently of the rest of the nasal dilator 10. The slots 98*a*, 98*b* in the substrate 20, the lower resilient member 14, the adhesive layer 34, and the release film 36, may be formed at the same time, for example by stamping, when the nasal dilator 90 is fully assembled, or, alternatively, may be formed into each layer individually.

The configurable hooks 92 may include two generally "L" shape substrate layers 100, 102, at least one of which has an adhesive on one side of the layer. Support members 97, similar to the support members 63 described above, may be held between or sandwiched by the two substrate layers 100, 102. Once attached to the nasal dilator 90, the configurable hooks 92 may be inserted into the nostril and bent to mechanically reduce or inhibit nostril collapse.

It will be appreciated that multiple variations of the nasal dilator described herein may be used to dilate the nasal valve and/or nostrils and/or prevent nostril collapse. For example, any of the nasal dilators 10, 40, 60, 90 may be separable such that the upper resilient member 12 and the lower resilient member 14 (inclusive of tabs and/or hooks 62 or 92, if present) may be used separately from one another. The upper resilient member 12 and lower resilient member 14 also may not be attached to one another by a portion of the substrate 26, and instead, be attached separately or independently to the nose to dilate one or both of the nasal valves or the nostrils. The separate layers of the dilator also may be attached to one another by melting, welding, or sewing the layers, or in any other manner as will be appreciated by one of skill in the art.

In another embodiment, the tabs 42 and/or hooks 62 or 92 may be secured to the nose with an adhesive bridge that laterally spans across the mid-line portion 15 of the nose. The adhesive bridge may be made from, for example, the substrate 20 and adhesive. The adhesive bridge may be configured for placement across the nasal vestibule, across the bony portion of the nose in the location of the nasal valve, some other location, or both. A resilient member, such as the resilient member 12 or 14, may be added to the adhesive bridge to provide additional dilation and/or support to the nose.

As one example, FIGS. 12-15 show that the nasal dilator may have only an upper resilient member 12 or upper adhesive bridge spanning across a mid-line portion 15 of the nose to dilate the nasal valve and adhesive tabs extending downwardly towards the nostril entrance for reducing or minimizing nostril collapse, as described above.

As another example, FIGS. 16-19 show that the nasal dilator may have a lower adhesive bridge or lower resilient member 14 for spanning across a lower portion of the nose and transversely across the mid-line portion of the nose 15 for dilating and/or supporting the nostrils. In another embodiment, the lower adhesive bridge or resilient member 14 may have adhesive tabs 42 extending downwardly towards the nostril entrance to reduce or inhibit nostril collapse, as described above.

As another example, FIGS. 20-31 show that an adhesive bridge over the nasal vestibule or nasal valve may have bendable hooks or adhesive hooks extending downwardly towards the nostril entrance for insertion into the nostril to mechanically reduce or inhibit nostril collapse, as described herein. The bendable hooks also may be configurable, as described above, to allow for their removal, and to allow the user to manipulate the hooks to achieve increased comfort and/or effectiveness. Additionally, a resilient member may be incorporated into the adhesive bridge as described above, to dilate the nostrils and/or nasal valve.

It is understood that equivalents and modifications to the foregoing embodiments will occur to others skilled in the art upon the reading and understanding of the specification.

What is claimed is:

1. A nasal dilator adapted for temporary attachment to a nose of a person comprising:

an upper elongate resilient member;

a lower elongate resilient member separate from the upper resilient member; and a flexible substrate for holding the upper resilient member and lower resilient member with respect to each other such that the upper resilient member is arranged to act upon the nose independently of the lower resilient member, the substrate having an upper portion secured to the upper resilient member and a lower portion secured to the lower resilient member, the upper resilient member and the lower resilient member each longer than a portion of the substrate connecting the upper and lower portions; and adhesive on a user-side of the nasal dilator for achieving the temporary attachment;

wherein, when the nasal dilator is attached to the nose, the upper resilient member applies a dilating force to an internal nasal valve of the user and the lower resilient member independently applies a dilating force to an external nasal valve of the user;

wherein a center portion of the lower elongate resilient member and a center portion of the upper resilient member are closer to one another than respective lateral ends of the lower resilient member are from respective lateral ends of the upper resilient member, such that when the nasal dilator is attached to the nose, the lateral ends of the lower resilient member extend in a direction from above the lobule of the user towards respective nostril openings; and further comprising a pair of downwardly extending bendable hooks connected to the lower portion of the substrate and each hook adapted for insertion into a nostril of the person to reduce nostril collapse, wherein the bendable hooks include elongate support members which are retained by corresponding fingers of the substrate.

2. The nasal dilator of claim 1, wherein the upper resilient member is an elongate shape adapted to span transversely across a mid-line of the nose.

3. The nasal dilator of claim 2, wherein the upper resilient member is substantially rectangular.

4. The nasal dilator of claim 1, wherein the lower resilient member is an elongate shape adapted to span transversely across a mid-line of the nose.

5. The nasal dilator of claim 4, wherein the lower resilient member is an arch shape.

6. The nasal dilator of claim 5, wherein the upper resilient member is substantially rectangular.

7. The nasal dilator of claim 1, wherein the portion of the substrate connecting the upper portion and the lower portion is frangible to allow the upper portion of the substrate to be separated from the lower portion of the substrate.

8. The nasal dilator of claim 1, wherein a user-side surface of each of the resilient members is adapted to curve away from the nose when the nasal dilator is not attached temporarily to the nose.

9. The nasal dilator of claim 1, wherein the adhesive is on adjacent lateral ends of the upper portion and the lower portion of the substrate, and no adhesive is on the user-side of the nasal dilator at a mid-line region.

10. The nasal dilator of claim 1, further comprising tabs having an adhesive on a back surface of the tabs, the tabs extending downwardly from the lower portion of the substrate and each adapted for respective engagement to sides of the nasal vestibule immediately adjacent nostril openings of the person.

11. A nasal dilator adapted for temporary attachment to a nose of a person comprising:
    a first resilient member that is adapted to dilate one of an internal nasal valve or an external nasal valve of a person;
    an adhesive bridge adapted to span transversely across a mid-line of the nose, the adhesive bridge forming a substrate for the first resilient member;
    adhesive on a user-side of the adhesive bridge, the adhesive for achieving the temporary attachment; and
    a pair of downwardly extending bendable hooks, each having a flat support member that is thinner than wide, the bendable hooks connected to the adhesive bridge via corresponding fingers and adapted to be bent by the person so that each support member wraps around outer skin of respective nostril openings of the person and into respective nostrils, wherein the support members retain the bent configuration established by the user so as to reduce nostril collapse.

12. The nasal dilator of claim 11, further comprising a second resilient member adapted to dilate the other of the internal nasal valve or the external nasal valve, wherein the adhesive bridge further forms a substrate for the second resilient member.

13. The nasal dilator of claim 12, wherein the substrate has an upper portion for holding the resilient member that is adapted to dilate the internal nasal valve and a lower portion to hold the resilient member adapted to dilate the external nasal valve.

14. The nasal dilator of claim 13, wherein the resilient members are each longer than a portion of the substrate connecting the upper portion to the lower portion of the substrate.

15. The nasal dilator of claim 14, wherein the portion of the substrate connecting the upper portion and the lower portion is frangible to allow the upper portion of the substrate to be separated from the lower portion of the substrate, thereby separating the first resilient member from the second resilient member.

16. The nasal dilator of claim 11, wherein a portion of the user-side of each bendable hook is adapted for insertion into the nostrils, and wherein such portions are adhesive free.

17. The nasal dilator of claim 11, wherein each respective hook engages a respective middle portion of an alar rim of a respective nostril of the person so as to reduce nostril collapse.

* * * * *

UNITED STATES PATENT AND TRADEMARK OFFICE
CERTIFICATE OF CORRECTION

| | | |
|---|---|---|
| PATENT NO. | : 8,047,201 B2 | Page 1 of 1 |
| APPLICATION NO. | : 11/380460 | |
| DATED | : November 1, 2011 | |
| INVENTOR(S) | : Bahman Guyuron et al. | |

It is certified that error appears in the above-identified patent and that said Letters Patent is hereby corrected as shown below:

Title page, Item (73), Assignee, replace "Innovation Alley Design, LLC," with -- Innovation Medical Equipment, LLC, --.

Signed and Sealed this
Fifteenth Day of May, 2012

David J. Kappos
*Director of the United States Patent and Trademark Office*